United States Patent [19]
Vangsness

[11] Patent Number: 5,713,843
[45] Date of Patent: Feb. 3, 1998

[54] SPONGE APPLICATOR WITH FLUID BALL

[75] Inventor: Todd S. Vangsness, Arlington Heights, Ill.

[73] Assignee: Allegiance Corporation, McGaw Park, Ill.

[21] Appl. No.: 696,278

[22] Filed: Aug. 13, 1996

[51] Int. Cl.⁶ ............................................. A61M 35/00
[52] U.S. Cl. ........................................... 604/3; 401/134
[58] Field of Search ............................ 604/1–3; 401/134

[56] References Cited

U.S. PATENT DOCUMENTS

| | | | |
|---|---|---|---|
| 4,206,843 | 6/1980 | Rainey | 604/3 |
| 4,507,111 | 3/1985 | Gordon . | |
| 4,578,055 | 3/1986 | Fischer | 604/3 |
| 4,747,719 | 5/1988 | Parkin | 604/3 |
| 4,854,760 | 8/1989 | Pike et al. | 604/3 |
| 4,995,344 | 2/1991 | Olson . | |
| 5,120,301 | 6/1992 | Wu | 604/3 |
| 5,265,620 | 11/1993 | Fisher | 604/3 |
| 5,266,266 | 11/1993 | Nason | 604/3 |
| 5,308,180 | 5/1994 | Pournoor et al. | 604/3 |

*Primary Examiner*—John G. Weiss
*Assistant Examiner*—Ki Yong O

[57] ABSTRACT

An applicator for delivering liquids or gels to solid surfaces. It comprises a liquid or gel filled hollow flexible bulb having a top and bottom. There is an opening in the bottom of the bulb containing a rupturable seal. A spike is fitted within the hollow bulb. This spike is positioned vertically above the rupturable seal and is capable of rupturing the seal in response to the application of downward pressure on the top of the bulb.

There is also present a sponge attachment plate having a top and a bottom which are connected by a channel. The top of the channel engages the opening in the bottom of the bulb. The bottom of the channel is in fluid communication with a sponge secured to the bottom of the sponge attachment plate. The applicator is particularly useful for delivering gelled antimicrobial products to localized areas of the body.

14 Claims, 3 Drawing Sheets

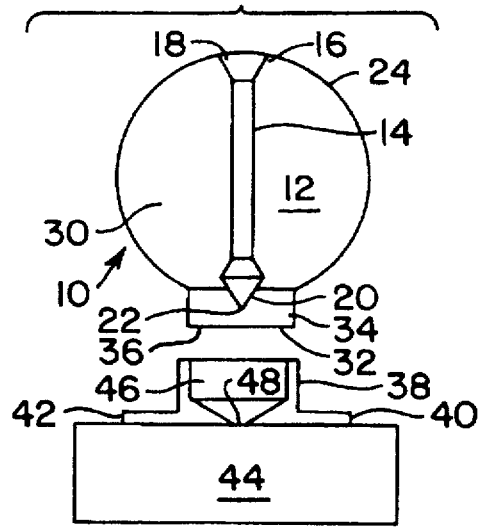
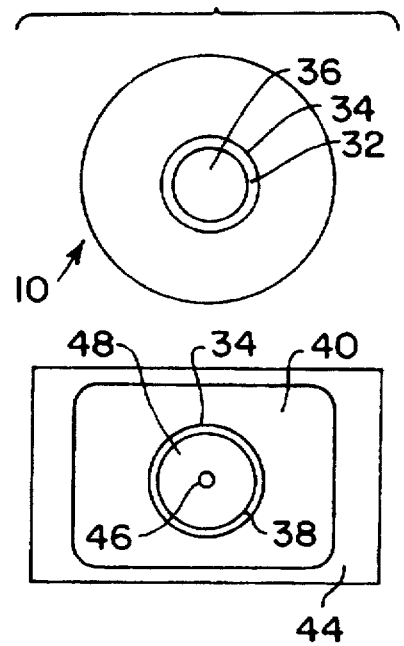
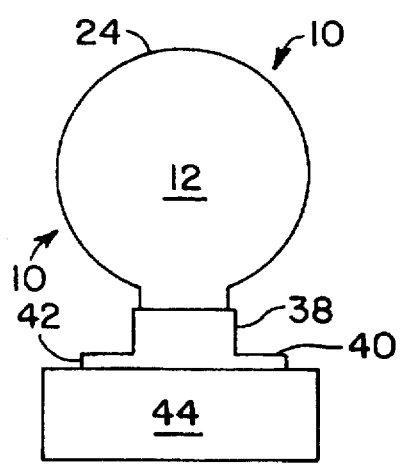
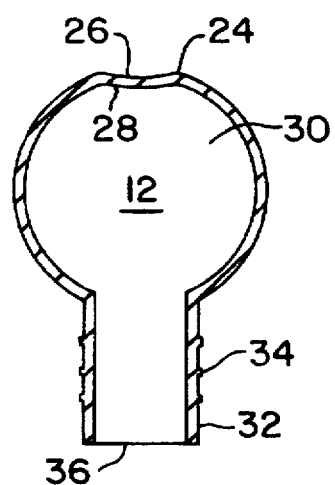
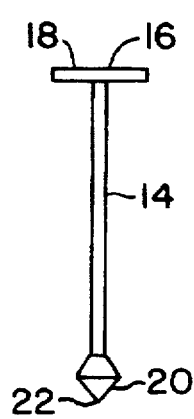

5,713,843

1

SPONGE APPLICATOR WITH FLUID BALL

FIELD OF THE INVENTION

The invention relates to applicators for applying liquids and gels to solid surfaces. More specifically, it provides applicators used to apply gelled antimicrobial agents to localized areas of the body.

BACKGROUND OF THE INVENTION

There are now available several reservoir fed sponge applicators for applying liquids to a variety of surfaces. These applicators have the advantage that the liquid to be applied and the sponge are one hand held unit. A specific form of these devices are those used to apply antiseptics to body parts. Typically, antiseptic preparation of surgery patients includes a preliminary scrubbing followed by the application of water soluble antiseptic paint solutions which are applied using sponge applicators of the type described above. Gel form antiseptics are usually applied using bottles, basins, cloths or hand held sponges.

These prior art applicators as presently available are incapable of applying viscous liquid or gel antiseptics in a convenient manner. Also, prior art applicators become uncomfortable to hold for long periods of use and they require excessive force when used to apply viscous liquids.

It would be an advance in the art of sponge applicators if an applicator were available which was capable of applying a variety of liquids and gels, was easy to use and was of unitary construction. Also beneficial would be an applicator which required little force and yet was easy to hold. Of further benefit would be an applicator which contained in a sealed sterile section antiseptic which could be released easily at the time it was to be applied.

THE INVENTION

The invention comprises an applicator for delivering liquids or gels to solid surfaces. The invention is particularly suited to deliver viscous liquids and gels such as complexed iodine gels. It comprises a liquid or gel filled hollow flexible bulb having a top and bottom. There is an opening in the bottom of the bulb containing a rupturable seal. A spike is fitted within the hollow bulb. This spike is positioned vertically above the rupturable seal and is capable of rupturing the seal in response to the application of downward pressure on the top of the bulb.

There is also present a sponge attachment plate having a top and a bottom which are connected by a channel. The top of the channel is attached to the opening in the bottom of the bulb. The bottom of the channel permits fluid to contact a sponge secured to the bottom of the sponge attachment plate. The applicator is particularly useful for delivering gelled iodine products to localized areas of the body.

In preferred embodiments of the invention the bulb is in the shape of a ball. In one embodiment the top of the ball is flat or indented which allows the thumb of the user to apply downward pressure to the bulb which motion activates the device. This flat top configuration also permits reception of a flat horizontal plate which is attached to the top of the spike.

The bottom of the bulb may contain a collar to which is fitted the rupturable seal. In a desirable embodiment of the invention, the interior of the collar contains a unitary spike assembly comprising a sealing ring which is fitted to a sleeve within which is centrally mounted the tip end of the spike by means of flexible arms. The top of the channel in the sponge

2 attachment plate contains a sleeve which is sized to engage in liquid sealing relationship the collar attached to the bulb. The channel located in the sponge attachment plate is desirably tapered downwardly from top to bottom to accommodate a corresponding taper formed onto the bottom of the spike. This arrangement allows efficient application of gel form medications and antiseptics contained in the bulb. The invention is especially useful in the application of iodine gel topical antiseptics to localized parts of the body.

BRIEF DESCRIPTION OF DRAWINGS

The drawings comprise:

FIG. 1 which is a vertical, cut away, exploded view of the bulb containing the spike and the sponge attachment plate and sponge fitted thereto.

FIG. 2 is a full bottom view of FIG. 1.

FIG. 3 is a vertical view of the assembled components of FIGS. 1 and 2.

FIG. 4 is a vertical cut away view which shows a ball shaped bulb having a flat top.

FIG. 5 is a vertical view of a spike which is designed for attachment inside the bulb illustrated in FIG. 4.

In the drawings like parts have like numbers.

DETAILED DESCRIPTION OF THE INVENTION

Figure 8:
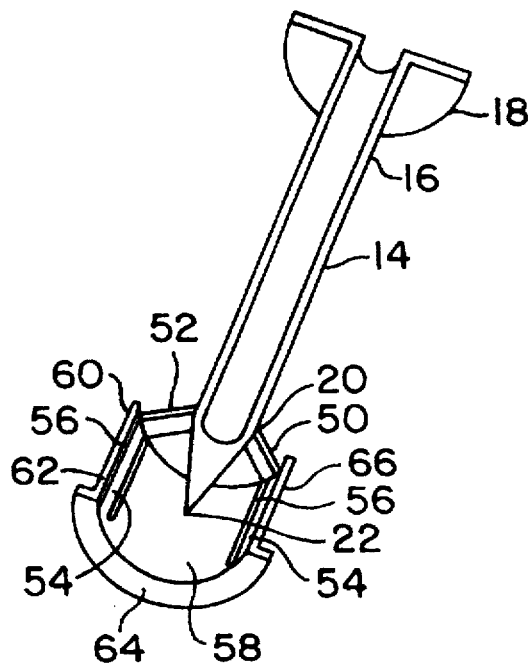
FIG. 8 is a cut away perspective view of a preferred embodiment showing the details of the unitary spike shown in FIGS. 6 and 7.
Figure 9:
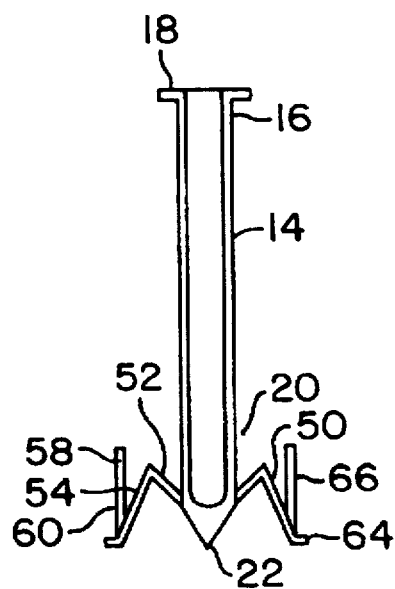
FIG. 9 is a vertical cut away view of the spike in the depressed mode which causes flexing of its mounting arms.

With respect to the drawings there is shown in FIGS. 1, 2 and 3 the applicator of the invention which is designated generally by the numeral 10. It comprises a hollow flexible bulb 12 within which is contained a vertically positioned spike 14. Spike 14 preferably will contain at its top 16 a flange which in one embodiment may be a mounting flange 18. The bottom 20 of spike 14 is pointed and as shown in FIGS. 15, 8 and 9 is cone shaped, which feature is designated by the numeral 22.

Figure 6:
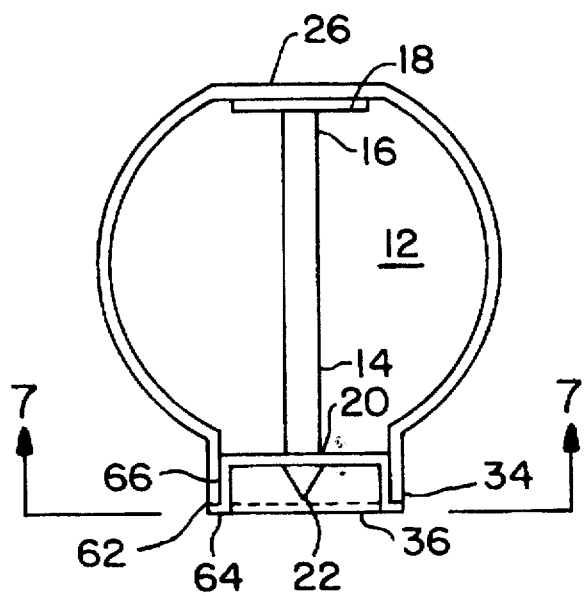
FIG. 6 is a cut away vertical view of the bulb containing a unitary spike assembly which prevents the spike from puncturing the bottom of the applicator.
Figure 7:
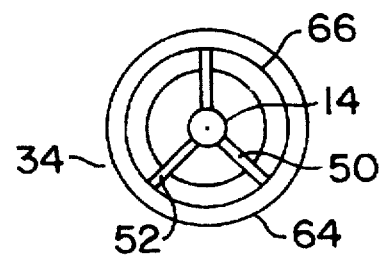
FIG. 7 is a bottom view taken along the lines 7—7 of FIG. 6.

As shown in all of the drawings the bulb is depicted as being ball shaped, which represents a preferred embodiment of the invention. As shown in FIGS. 4 and 6 the top 24 of bulb 12 is flat which feature is designated by the numeral 26. This feature is provided primarily to make the applicators easy to depress by using thumb pressure. The flat flange 18 depicted in FIG. 5 may be adhesively bonded or attached by other fastening methods to the interior face 28 of flat top 24.

The hollow interior of the bulb 12 is identified by the numeral 30. Positioned vertically within the hollow interior 28 of bulb 12 is spike 14 which is dimensioned so that its bottom 20 is slightly above bottom 32 of bulb 12. As shown to best advantage in FIGS. 1 and 2 at the bottom 32 of bulb 12 is bulb collar 34, which in the case of these views is constructed so that if forms a part of the bulb. In FIG. 4 collar 34 is shown as being ribbed, which is an optional feature, and is constructed of the same flexible material as bulb 12. The bottom of collar 34 is fitted with a rupturable seal 36. This arrangement allow a sterile liquid to be contained in the device without contamination.

A preferred ball and spike assembly is shown in FIGS. 6,7,8 and 9. In these drawings the spike is a one piece unit and may be constructed using injection molding. Its bottom 20 is fitted with a plurality of arms 50 which as shown in the drawings are three in number. Arms 50 are comprised of shoulders 52 and legs 54. The legs 54 are contained within slots 56 in sleeve 60 the interior of which is designated by numeral 58. The bottom 62 of sleeve 60 terminates and rests upon sealing ring 64 which together with the outside 66 of sleeve 60 are dimensioned to slide into collar 34 of bulb 12 and mate with the bottom 32 of the bulb. This is shown clearly in FIG. 6. The sealing ring 64 is bonded to the bottom of collar 34 by using such techniques spin welding or hot melt gluing.

The entire spike assembly shown in FIGS. 8 and 9 are constructed of semi rigid to rigid plastic materials which allows the shoulders 52 and legs 54 of arms 50 to flex when downward pressure is exerted on flange 18 of spike 14. This flexing action is shown in FIG. 9. By being a part of sleeve 60 and centered therein by means of arms 50 the spike's downward motion in limited. This insures that the spike will not penetrate through the entire unit and touch the patient. The hinging action of the arms 50 guide and insure that the downward thrust of the spike is parallel to the inside 58 of sleeve 60. As shown in FIG. 6 spike 14 is of sufficient length so that flange 18 is positioned directly below flat top 26 of bulb 12.

Collar 34 is adapted to slidably engage and be attached to sleeve 38 which forms the top of sponge attachment plate 40. The bottom 42 of sponge attachment plate 40 is attached to sponge 44. In approximately the center of sponge attachment plate 40 and extending there through is channel 46. In a preferred embodiment the bottom of channel 46 is tapered which feature is identified by the numeral 48. This taper is dimensioned to mate with cone shaped tip 22 of spike bottom 20. Importantly, this taper allows the flow of gels applied by the applicator to be easily controlled.

Figure 10:
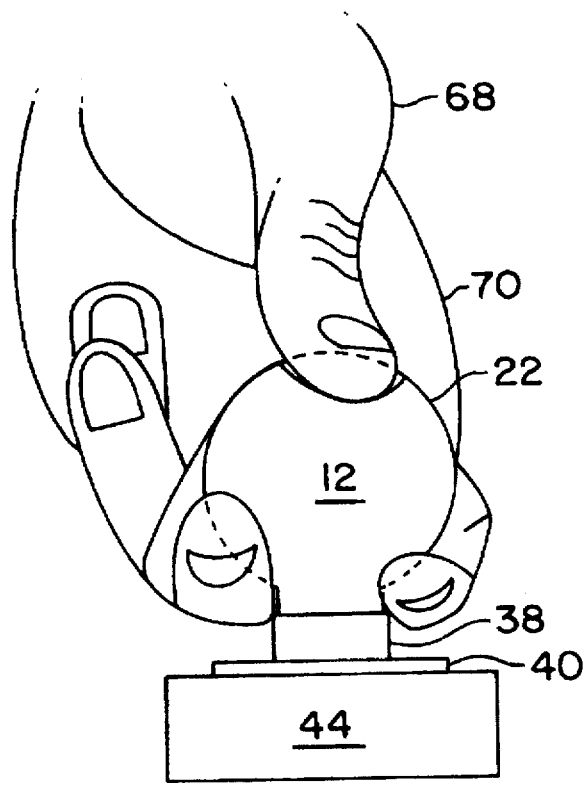
FIG. 10 is a vertical view showing a hand applying downward pressure on the bulb to allow the spike within the bulb to puncture a rupturable seal which is located in the bottom of the bulb.
Figure 11:
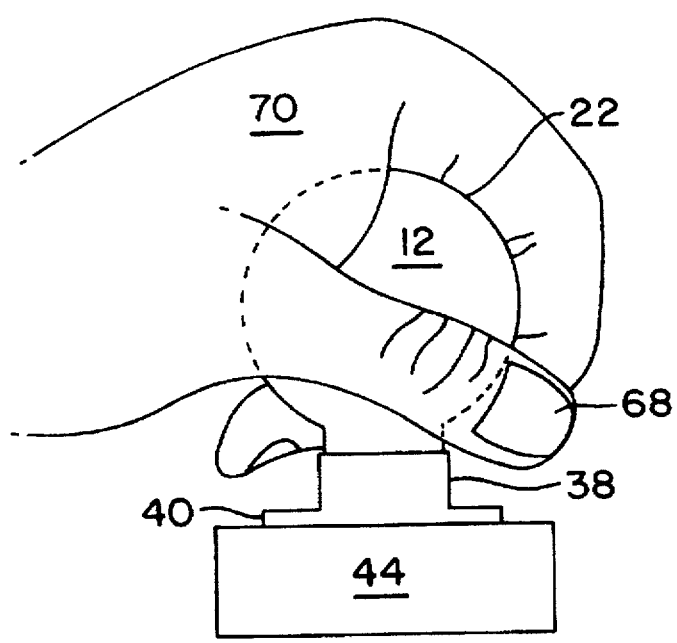
FIG. 11 is a vertical view of a hand squeezing the bulb either to release its contents to a sponge or to prep a patient with an already gel loaded sponge.

The hollow interior 30 of bulb is filled with a liquid or a gel such as a complexed iodine gel and is retained within the interior by means of rupture seal 36. As shown in FIG. 10 the thumb 68 of hand 70 is applying downward pressure on the top 24 of bulb 12. This forces the spike 14 to engage and pierce rupture seal 36. Once so pierced, thumb pressure is released allowing the bulb to re-expand and the tip 22 of spike 14 disengages itself from channel 38. The bulb is squeezed as shown in FIG. 11 one or more times causing the liquid or gel within the bulb to flow into channel 46 and through the sponge 44.

Sponge 44, as shown in the drawings, is of larger dimension than the sponge attachment plate 40. This represents another preferred embodiment of the invention since the sponge 44 being flexible is more easily capable of reaching confined, curved or angled surfaces. This is important when the applicator 10 contains iodine antiseptic gel and is used to disinfect body parts.

The bulb is preferably constructed of a vinyl plastic such as polyvinyl chloride or polyolefin plastics such as polyethylene, polypropylene and like polymers. The spike and the sponge attachment plate may be constructed from high density polyethylene or polypropylene. Polyurethane sponges provide a good delivery medium for gels. The rupture seal may be fabricated from suitable plastics, foils or combinations thereof. It is understood, however, that the materials of construction may vary, and the invention is not intended to be thus restricted.

While the applicator of the invention is capable of delivering to solid surfaces liquids and gels it is most useful in delivering viscous liquids and gels to the skin. It is particularly useful when used to apply iodine gels, to parts of the human body. The term viscous liquid and gels as used herein is meant to cover any liquid or gel capable of flow which has a specific gravity of at least 1. Preferably, the specific gravity is greater than 1.5. The term, sponge, is intended to include any porous substrate that can apply a liquid or gel freely.

The applicator is ideally suited for the application of gels to solid surfaces. When it is used to apply antiseptics to the body the applicator is easy to hold and use. Prior art applicators would require excessive force to deliver gels. Only one hand is needed to activate and use the applicator herein described. By using this applicator it is possible to eliminate bottles, caps, basins and individual sponges or cloth applicators when applying antiseptics. Also, this applicator does not require glass ampoules in its design and construction.

To summarize the several advantages of the invention the following are presented:

Ergonomically correct.

Allows the user to angle and position their hands in a comfortable position.

Only one hand is needed to use the applicator.

Little force is required to hold or use the device.

It is a unitary device.

Flow cost materials may be used in its fabrication.

It reduces prepping time.

Flow control is easily regulated.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

I claim:

1. An applicator for delivering liquids or gels to solid surfaces comprising:
    (a) a liquid or gel filled hollow flexible ball shaped bulb having a top and bottom;
    (b) an opening in the bottom of the bulb containing a rupturable seal;
    (c) a spike within the hollow bulb positioned vertically above the rupturable seal and being capable of contacting and rupturing the seal in response to the application of downward pressure on the top of the bulb;
    (d) a sponge attachment plate having a top and a bottom connected by a channel with the top of the channel engaging the opening in the bottom of the bulb and bottom of the channel being in fluid communication with;
    (e) a sponge secured to the bottom of the sponge attachment plate which sponge is of larger dimension than the sponge attachment plate.

2. The applicator of claim 1 wherein the opening in the bottom of the bulb includes a collar adapted to mate in liquid sealing relationship with a sleeve fitted to the top of the channel of the sponge attachment plate.

3. The applicator of claim 1 wherein the channel in the sponge attachment plate and the spike are tapered.

4. The applicator of claim 2 wherein the rupturable seal is attached to the collar on the bottom of the bulb.

5. The applicator of claim 1 wherein the top of the bulb is flat and contains attached to the interior thereof a horizontal plate attached to the top of the spike.

6. An applicator for delivering iodine gels to localized areas of the body comprising:

(a) an iodine gel filled hollow flexible ball having a top and bottom;

(b) an opening in the bottom of the ball containing a collar fitted with a rupturable seal;

(c) a spike within the hollow bulb positioned vertically above the rupturable seal which is capable of rupturing the seal in response to the application of downward pressure on the top of the bulb;

(d) a sponge attachment plate having a top and a bottom connected by a channel with the top of the channel containing a sleeve for engaging in liquid sealing relationship the collar in the bottom of the bulb and bottom of the channel being in fluid communication with;

(e) a sponge secured to the bottom of the sponge attachment plate.

7. The applicator of claim 6 wherein the channel in the sponge applicator plate and the spike are tapered.

8. The applicator of claim 6 wherein the top of the ball is flat and contains attached to the interior thereof a horizontal plate attached to the top of the spike.

9. An applicator for delivering liquids or gels to solid surfaces comprising:

(a) a liquid or gel filled hollow flexible bulb having a top and bottom;

(b) an opening in the bottom of the bulb on which is mounted a unitary spike assembly which comprises:
 (1) a sealing ring having top and bottom faces;
 (2) a rupturable seal on the bottom of the sealing ring;
 (3) means attaching the sealing ring to the bottom of the opening of the bulb;
 (4) a sleeve mounted on the top face of the sealing ring which sleeve has an outside which slidably fits into the opening in the bottom of the bulb;
 (5) flexible arms attached to the inside of the sleeve and near the bottom of a spike for centering the spike vertically above the rupturable seal which spike contains at its top a flange which is positioned beneath the top of the bulb;
 (6) which spike assembly is capable of rupturing the seal in response to the application of downward pressure on the top of the bulb;

(c) a sponge attachment plate having a top and a bottom connected by a channel with the top of the channel engaging the opening in the bottom of the bulb and bottom of the channel being in fluid communication with;

(d) a sponge secured to the bottom of the sponge attachment plate.

10. The applicator of claim 9 wherein the bulb is ball shaped.

11. The applicator of claim 9 wherein the opening in the bottom of the bulb contains a collar adapted to mate in liquid sealing relationship with a sleeve fitted to the top of the channel of the sponge attachment plate.

12. The applicator of claim 9 wherein the channel in the sponge applicator plate and the spike are tapered.

13. The applicator of claim 9 wherein the arms comprise a plurality of shoulders and legs.

14. The applicator of claim 13 wherein the legs are attached to slots positioned within the sleeve.

* * * * *